United States Patent
Orlich

(12) 
(10) Patent No.: US 6,171,307 B1
(45) Date of Patent: Jan. 9, 2001

(54) BONE STABILIZER AND METHOD

(76) Inventor: José Luis Orlich, Clinica Orlich, Avenida Central, Calle 16, San José(CR)

( * ) Notice: Under 35 U.S.C. 154(b), the term of this patent shall be extended for 0 days.

(21) Appl. No.: 09/506,050

(22) Filed: Feb. 17, 2000

(30) Foreign Application Priority Data

May 28, 1999 (CR) .......................................................... 5992

(51) Int. Cl.$^7$ ................................................. A61B 17/56
(52) U.S. Cl. ................................ 606/53; 606/54; 606/57; 606/58
(58) Field of Search .................................. 606/53, 54, 55, 606/56, 59, 57, 58, 61, 105; 602/5, 16, 20, 23

(56) References Cited

U.S. PATENT DOCUMENTS

| | | | | |
|---|---|---|---|---|
| 2,250,417 | * | 7/1941 | Ettinger | 606/54 |
| 2,371,519 | * | 3/1945 | Haynes | 606/53 |
| 5,601,551 | * | 2/1997 | Taylor et al. | 606/54 |
| 5,662,648 | * | 9/1997 | Faccioli et al. | 606/54 |
| 5,769,851 | * | 6/1998 | Veith | 606/57 |

\* cited by examiner

*Primary Examiner*—Pedro Philogene
(74) *Attorney, Agent, or Firm*—Jack E. Dominik

(57) ABSTRACT

An apparatus and procedure for the external unilateral fracture fixation, fracture compression or enlargement of osseous tissue with a metal or equivalent material slotted forked stick to hold and position the threaded pins in its length, inserted in the bone with multiple fastening slid able screws and their bolts to attach the pins to the slotted forked stick, a solid slid able cube to hold and position the slotted forked stick, a supporting axial bar, and an axial threaded bar. A preferred embodiment includes at least three slotted forked sticks that hold and fix, with the use of compression screws and their bolts, threaded pins that penetrate the proximal and distal fragments of the bone through both corticals. A preferred embodiment includes slotted forked sticks that adapt to the threaded pins, introduced in the bone, at any degree of inclination or orientation that these pins might have with respect to the bone. A preferred embodiment includes metal cubes that are mounted in the supporting axial bar that support and fix the slotted forked sticks allowing a rotational movement and displacement of the slotted forked stick to permit the positioning and fixation of the threaded pins in accordance with the orientation that they have been placed in the bone. A preferred embodiment includes a threaded axial bar with bolts that is held by a fixed stabilizing plate, and when it is fixed to the cubes, controls the compression or distraction of bone tissue by maneuvering the pins.

10 Claims, 6 Drawing Sheets

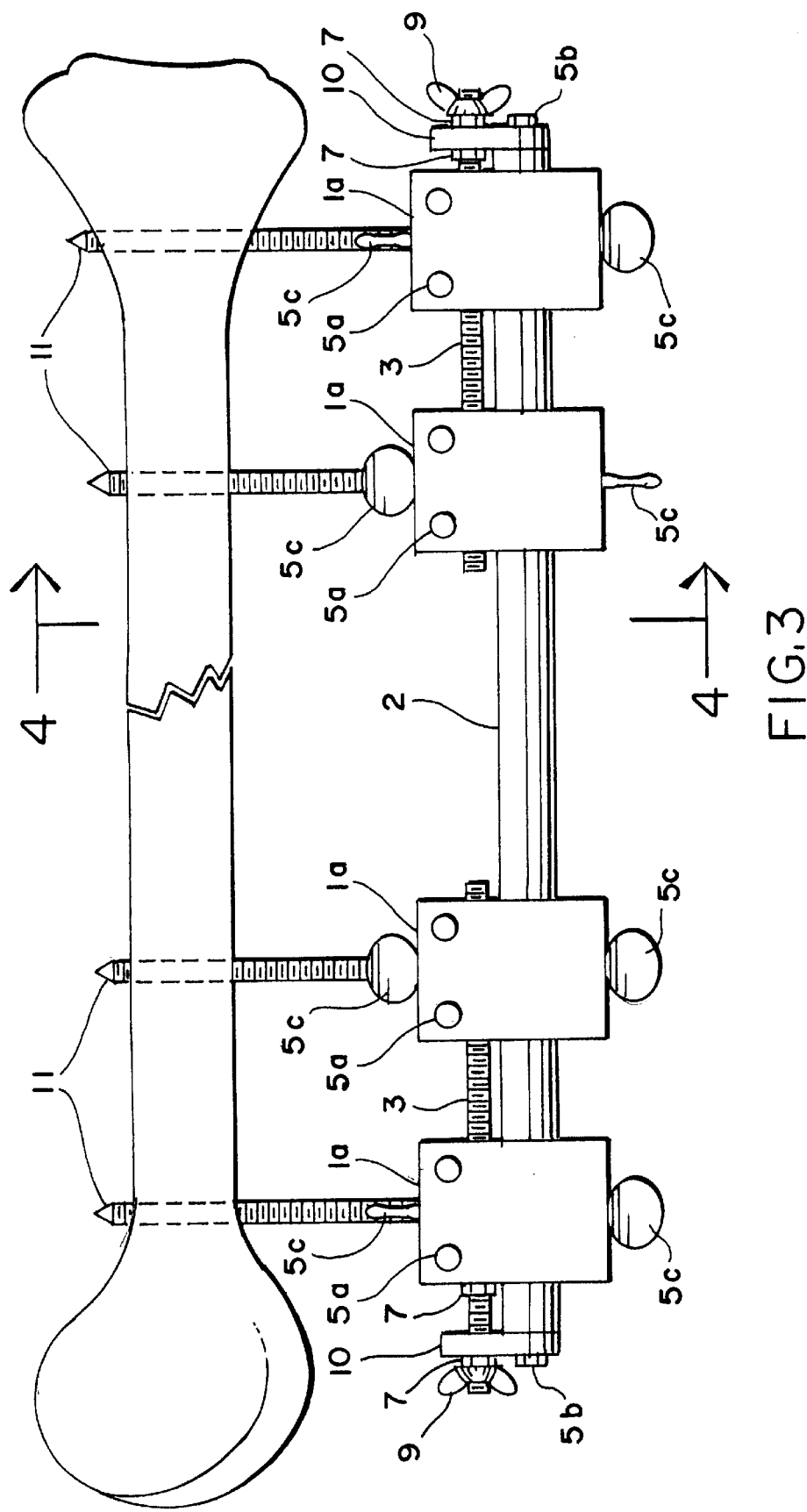

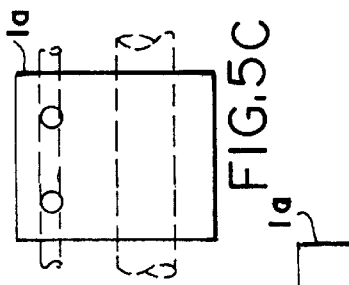
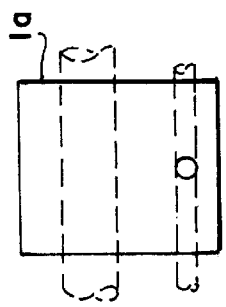
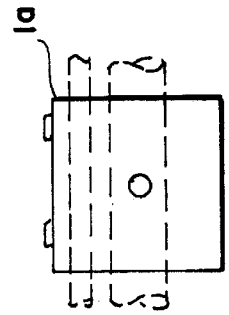
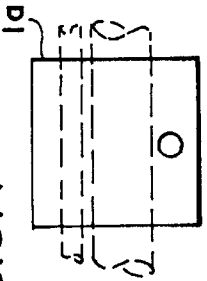
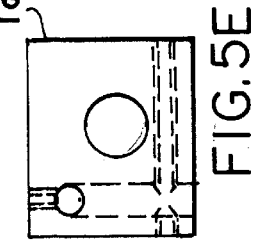
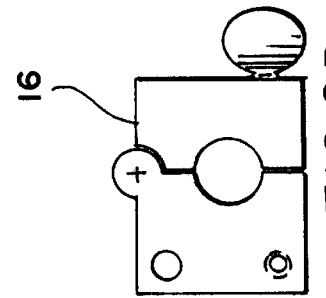
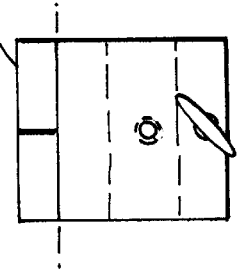
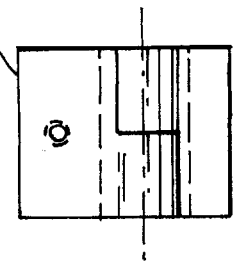
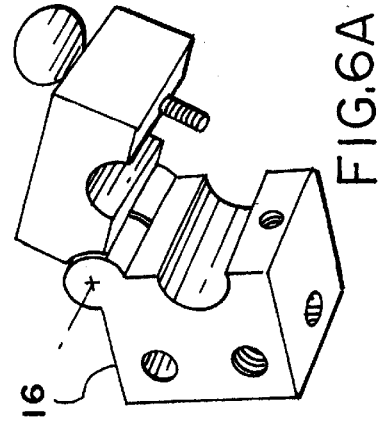
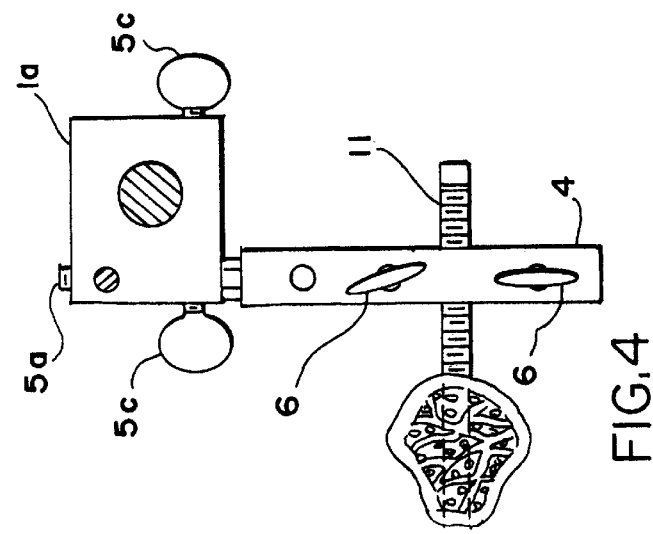

BONE STABILIZER AND METHOD

FIELD OF THE INVENTION

The field of invention relates to a bone setting apparatus and method for the external unilateral fracture fixation, compression or enlargement of human osseous tissue.

BACKGROUND OF THE INVENTION

Bone fractures have been traditionally treated by immobilization with a cast. Treatment has evolved and now the use of surgical procedures using intramedullary pins, plates, and screws have become common. These procedures require major surgery and immobilization. Any major surgery involves risks or infections and/or many other complications. Also the required post operatory treatment causes pain and discomfort to the patient.

The use of external fixators reemerged in the early sixties. Several types of mechanisms and procedures appeared in use with several important deficiencies in current technology:
the required use of templates
not cost effective
cumbersome to install
uncomfortable to the patient
not very versatile
current external fixators share one or more of the above characteristics.

SUMMARY OF THE INVENTION

The invention is based upon the use of an external rod, brace, or other stabilizing means to position and move bone pins which pass through the flesh into the bone during the healing process. Basically the apparatus and procedure are for the external unilateral fracture fixation, compression or enlargement of osseous tissue comprising: a) a metal or equivalent material slotted forked stick to hold and position threaded trans-osseous pins in its length; b) multiple fastening slidable screws with bolts to attach the threaded trans-osseous pins to the slotted forked stick; c) a solid slidable cube to hold and position the slotted forked stick; d) a supporting axial bar, and e) an axial movable bar with securing means.

The method begins with the insertion of trans-osseous pins in the osseous tissue. These pins are then positioned and fixed according to the state of the osseous tissue. The pins are held by clamping forks that are inserted in cubes that slide and are positioned along an axial bar. The pins are held by the clamping forks in accordance with the position in which they were inserted into the osseous tissue. The cubes are fixed along the axial bar make the clamping forks and the pins attached to them, immobilize, distract or compress the osseous tissue.

The primary object of the invention is to provide a fast and effective immobilization of bone fractures or enlargement of osseous tissue.

Another object of the invention is to provide a non opened reduction of bone fractures.

Another object of the invention is to provide a versatile treatment for diverse fractures.

A further object of the invention is to provide an external fixation of fractures without the use or need of templates.

Yet another object of the invention is to provide a cost effective alternative for bone fracture treatment.

Still yet another object of the invention is to provide a minimal surgery in case of extension or enlargement of osseous tissue when bone shortening or loss has occurred.

Another object of the invention is to provide a method for minimal disturbance of the hematoma formed at the fracture site and soft tissue disturbances which will eventually produce osseous calluses.

Another object of the invention is to provide a method to minimize fracture infections and other complications of mal-alignment of the fracture.

Another object of the invention is to fix the trans-osseous pins no matter the direction or inclination in which they are placed.

A further object of the invention is to provide a patient friendly device for fracture treatment.

Yet another object of the invention is to provide a lightweight device for fracture treatment or enlargement of osseous tissue.

Still yet another object of the invention is to provide a device that allows movement of adjacent articulations in bone fracture treatment or enlargement of osseous tissue.

DESCRIPTION OF THE DRAWINGS

Further objects and advantages of the present invention will become apparent as the following description proceeds, taken in conjunction with the accompanying illustrative drawings in which:

FIG. 2 is a view of the reverse side of the bone stabilizer shown in FIG. 1 illustrating how the cubes are moved along the stabilizer rod, whereas FIG. 1 illustrates how the forks are secured and the bone pins are secured;

FIG. 3 is a view perpendicular to that of FIGS. 1 and 2 illustrating how the pins penetrate the bone and can therefore be adjusted to lengthen or shorten the space at the fracture;

FIG. 4 is a transverse sectional view taken along section line 4—4 of FIG. 3 showing how the pin penetrates the bone and is secured in place by the forks;

FIGS. 5A, 5B, 5C, 5D and 5E are views of the illustrative cube 1a;

FIGS. 6A, 6B, 6C, and 6D are illustrative views of a hinged cube optionally employed and identified as 16 in FIG. 12;

DETAILED DESCRIPTION OF THE PREFERRED EMBODIMENTS

Figure 1:
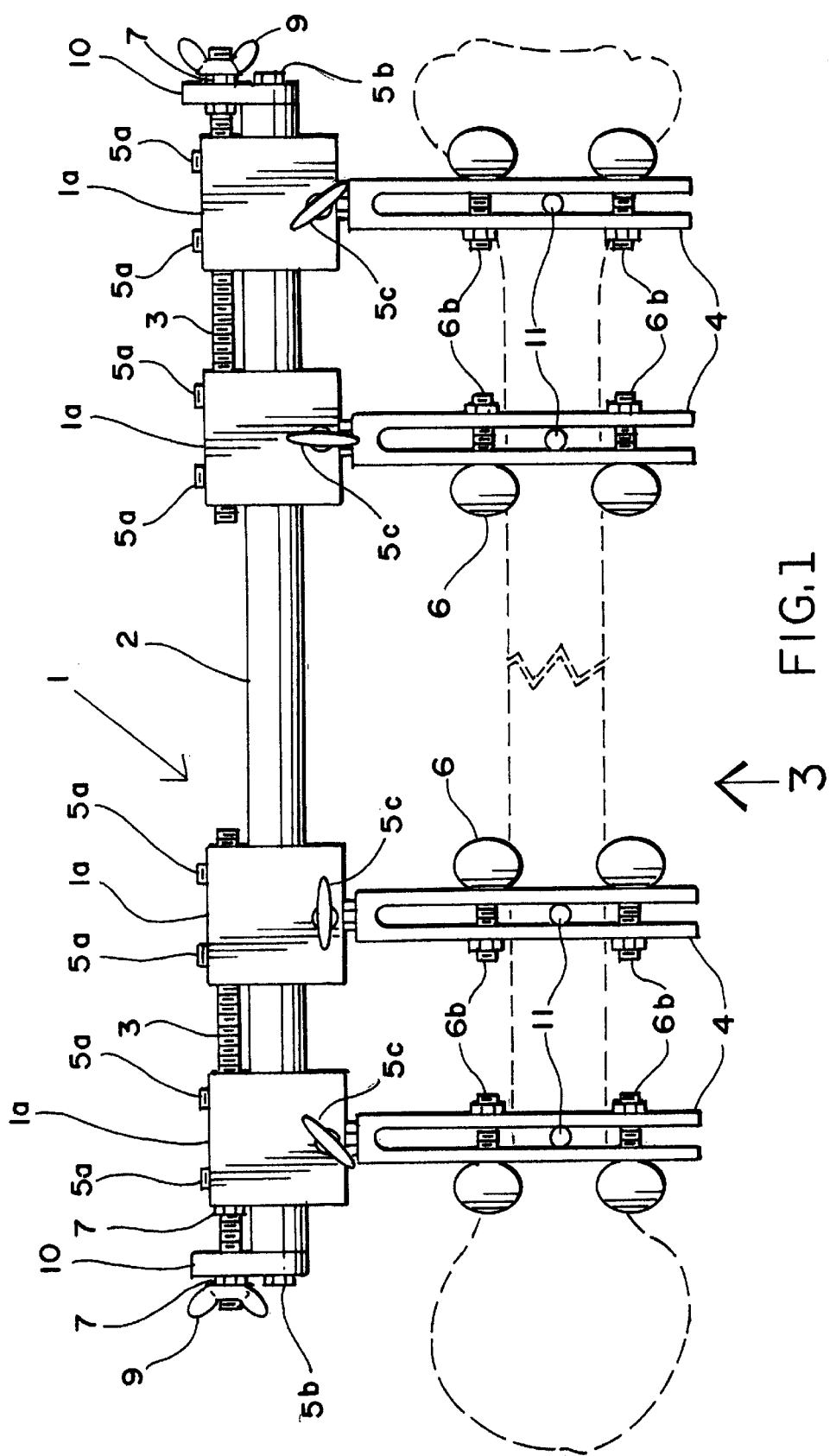
FIG. 1 is a plan view of the subject bone stabilizer showing the majority of the components and showing in phantom lines of a representative thigh bone or femur.
Figure 2:
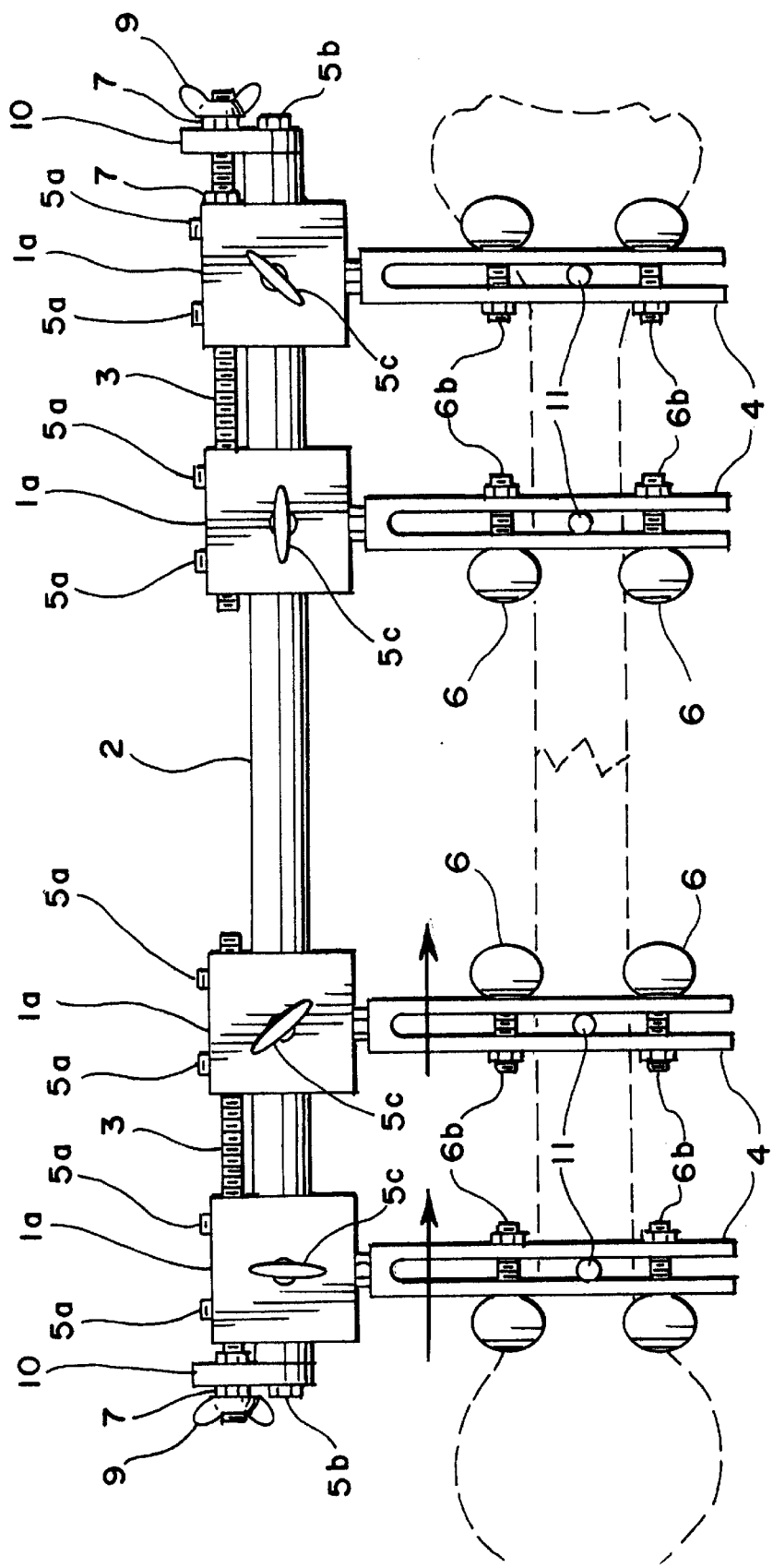
Figure 7:
FIG. 7 is a plan view of the mounting bar.
Figure 8A:
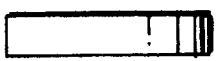
FIGS. 8A and 8B are a plan view and side view of the clamping fork.
Figure 8B:
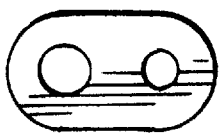
Figure 9A:
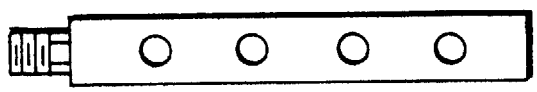
FIGS. 9A and 9B are plan and end views of the drive plate.
Figure 9B:
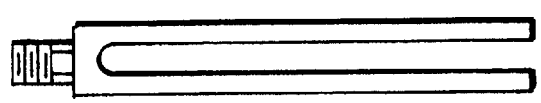
Figure 10:
FIG. 10 is a plan view of a typical bone pin.
Figure 11:
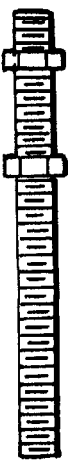
FIG. 11 is a plan view of the thread drive.

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

This apparatus and procedure contemplate the use of a metallic or functionally equivalent material device that is easily applied in the orthopedic and traumatologic fields and incorporates a procedure to immobilize and/or compress osseous fractures, elongate or distend osseous tissue. It replaces previous technology that consisted in the immobilization of the injury either with a cast, screws, metallic plates or intra medullar pins in fractures and trans osseous pins that distract or compress the osseous tissue when bone elongation or compression is required.

This present invention solves three technical problems: the first one is the one presented by the immobilization and alignment of osseous fractures, the second one is the compression of osseous tissue to accelerate the formation of osseous calluses for their speedy consolidation and the third one, the distension or elongation of osseous tissue in those cases where there is a need to elongate or distract the bone when bone shortening or loss has occurred.

In the first case fractures require physiologically and anatomically an absolute immobilization and good alignment for the formation of osseous callus for its total consolidation for a period of time long enough to allow the radiological verification of the fracture's stability. The illustrative stabilizer 1 holds, immobilizes and aligns both ends of the fracture by four or more cylindrical threaded pins 11 with sharp ends that penetrate the bone, with a variable pin diameter of 3 to 5 millimeters and a variable pin length, in accordance with the thickness of the extremity member, with a 10 centimeter average. The ends of these pins 11 are introduced inside the bone in the following way: two or more in the distal fragment and two or more in the proximal fragment of the fracture. Once the pins 11 have been inserted as described and shown in FIG. 3, and the fracture has been anatomically reduced, the pins 11 are immobilized and held in that position by clamping forks 4 with screws 5*b* and their bolts 6*b* to keep them in position. Once the clamping forks 4 have been positioned according to the inclination of the inserted pins 11 they are fixed to their corresponding cubes 1*a* with lock bolts 6 or at a hinged cube 16 to be placed in case another slotted clamping fork 4 is required. The cubes 1*a* have several threaded holes for the set screws 5*a* to fix them to the threaded device 3, another threaded hole to fix to the set nut 7 and one more to fix the clamping fork 4. The threaded drive that holds and aligns, has a variable length that depends on the length of the bone, typically between 20 and 30 centimeters.

Figure 12:
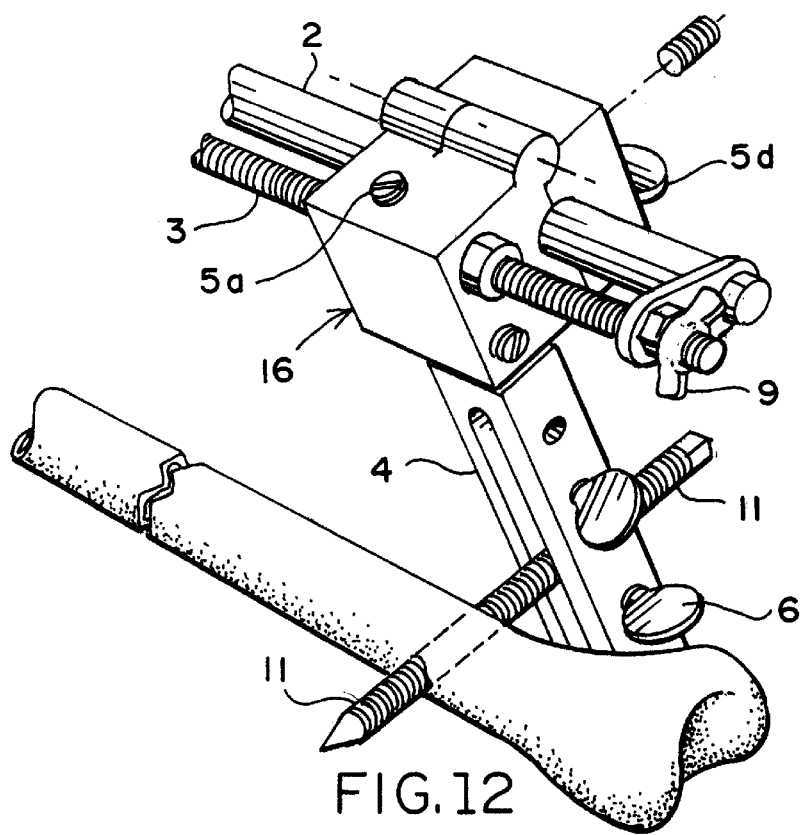
FIG. 12 is a perspective view of the use of the hinged cube in place.
Figure 13:
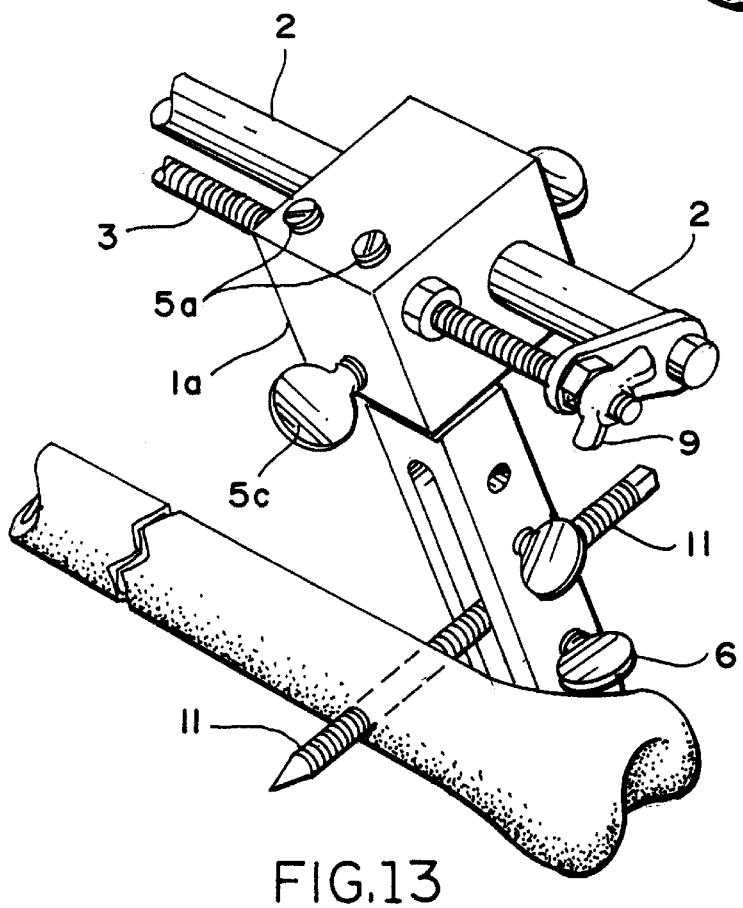
FIG. 13 is a perspective view of the standard cube in place.

The cubes 1*a* are positioned along the mounting bar 2 and threadedly engaged to the adjustment member during the original surgical procedure. Thereafter, the cubes 1*a* can be moved closer together, further apart, or remain stationary. During the course of some surgical procedures, it may prove desirable to add additional pins 11 to the bar 2, and after the initial surgery is completed. In order to do this, as shown in FIG. 6A and FIG. 12, the hinged cube 16 is provided which can be hingedly secured to the bar 2 and thereafter clampingly engaging the adjustment screw, and receiving a clamping fork 4 for positioning a further bone engaging pin where such additional support is needed. The clamping forks 4 are held in position with a thumb screw 5*c* to its corresponding cube to prevent any rotation.

In another application, the distraction of osseous tissue accelerates the formation of osseous callus, especially in the pseudo arthrosis or delayed consolidation cases. The stabilizer 1 moves in conjunction, either by compression or distraction, the cylindrical threaded pins 11 inserted in the bone and held by the clamping fork 4 through the holes in the cubes 1*a,* by the action of the thread drive 3 stabilized by a drive plate 10 that is located in one of the extremes of the drive bar 3. The compression or distraction action is achieved by the drive bar 3 assisted by the drive plate 10, fixed to the cubes 1*a*. This drive 3 controls the compression by means of a wing nut 9 on the outer face of the plate. When this set nut is screwed against the drive plate 10 it produces compression at the fractured site.

In yet another application, when bone elongation is required, the device functions in the following way: The bone is osteotomized at the desired level and held at each end with two or more pins 11, as described before for fractures and compression. The bone is elongated by a distraction of the osteotomized region stretching at a rate of 1 milimeter per day until the desired length is achieved. The procedure in this case is as follows: once the apparatus is assembled as described before, the threaded drive 3 that has been introduced in one or more cubes 1*a* and positioned with the drive plate 10, distracts the osteotomy by rotating the corresponding wing nut 9, which, located in the exterior face of the same drive plate 10, drives the plate outwardly, producing a distraction or separation of the osteotomized bone.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

It will be understood that various changes in the details, materials and arrangements of parts which have been herein described and illustrated in order to explain the nature of the invention, may be made by those skilled in the art within the principle and scope of the invention as expressed in the appended claims.

What is claimed is:

1. An apparatus and procedure for the external unilateral fracture fixation, fracture compression or enlargement of human osseous tissue by the use of threaded pins which penetrate the skin and bone comprising:

clamping fork to hold and position the threaded pins in its length;

multiple fastening slidable means with further means to attach the pins to the clamping fork;

a slidable member to hold and position the clamping forks;

supporting means for the adjustable alignment of the bone; and advancing and retarding means for compression or distraction of the bone;

whereby the fracture can be treated by extension, compression, or stabilization.

2. An apparatus and procedure, according to claim 1, for the external unilateral fracture fixation, fracture compression or enlargement of osseous tissue, further comprising at least three slotted forked sticks that hold and fix, with the use of compression screws, threaded pins with a sharp end that penetrate the proximal and distal fragments of the bone through both corticals of the bone.

3. An apparatus and procedure, according to claim 2, for the external unilateral fracture fixation, fracture compression or enlargement of osseous tissue, further comprising slotted clamping bars that adapt to the sharp ended pins, introduced in the bone, at any degree of inclination or orientation that these pins might have with respect to the bone.

4. An apparatus and procedure, according to claim 3, for the external unilateral fracture fixation, fracture compression or enlargement of osseous tissue, further comprising metal cubes that are mounted in the supporting axial bar that support and fix the clamping fork allowing a rotational movement and displacement of the clamping forks to permit the positioning and fixation of the threaded pins in accordance with the orientation that the pins have been placed in the bone.

5. An apparatus and procedure, according to claim 4, for the external unilateral fracture fixation, fracture compression or enlargement of osseous tissue, further comprising the means for moving the cubes along the supporting axial bar permitting the clamping forks to hold and position the bone pins to compress or distract the osseous tissue.

6. An apparatus and procedure, according to claim 5, for the external unilateral fracture fixation, fracture compression or enlargement in osseous tissue, further comprising of an axial threaded bar that goes through one or more cubes in order to displace the cubes along the length of the supporting axial bar by means of bolts that are screwed towards the stabilizing plate fixed in any end of the supporting axial bar in such a way that, when screwing the inner bolt, the osseous tissue of the fracture or osteotomy is compressed, and when the external bolt is screwed against the stabilizing plate, the osseous tissue is distracted or separated by the pins.

7. Bone setting apparatus by means of a bone penetrating pin which has a shank portion which is susceptible of movement substantially along the axis of the bone comprising, in combination, a stabilizing rod extending through and beyond the area of limb penetration intended for bone stabilization during bone growth at an interrupted area;

at least two adjustable members positioned adjustably along such stabilizing member;

each of said adjustable members having an extending clamp with opposed jaws for engaging a bone penetrating pin;

means for securing the bone penetrating pins by clamping in adjustable relationship with the stabilizing bar;

drive means connecting the two adjustable members having adjustment means there along to permit forceably bringing the pins closer together or extending the pins an increased distance, each from the other;

said adjustable members being movable longitudinally along the axis of the stabilizing rod, said extending clamp jaws being able to clamp the bone penetrating pin along a transverse axis perpendicular to the longitudinal axis and perpendicular to the plane of the longitudinal and transverse axis; and said two members and adjustable pin member being tri-axially adjustable;

whereby after manually setting the bone and determining its ultimate relationship to the area of interruption of the bone whereby the length of the total bone can be manipulated longitudinally, transversely and perpendicularly to the plane defined by the longitudinal and transverse axis during the healing process to stabilize, increase, or decrease the gap at the area of bone repair.

8. A method of bone stabilization during the healing process at an area of bone restoration comprising the steps of:

surgically preparing an area of restoration to either shortened, lengthened, or stabilize the gap at the area of restoration;

thereafter positioning a stabilization bar member essentially parallel with the bone structure and extending in both directions from the area of bone restoration;

positioning a plurality of bone pin penetrating members along the stabilization member at positions adjustable longitudinally along the stabilization member;

positioning clamps extending laterally from the bone stabilization member and clampingly engaging the bone pins to be driven into the bone and through the flesh and thereby stabilizing;

providing means for adjusting the space between the pins on either side of the area of restoration;

all of said members being adjustable to permit the bone pin to be positioned along three separate axis, away from or toward the stabilization bar, while longitudinally perpendicular to the stabilization bar capable of movement along the axis of the stabilization bar, and independently elevated or lowered from the clamping means; and ensuring tri-axial mobility of the pins and positioning clamps;

whereby the area of restoration can be either shortened, lengthened, or stabilized during the bone regrowth phase following the bone surgery.

9. In the method of bone stabilization according to claim 8, the additional step of:

providing hinged bone stabilization members which serve to clampingly engage the bone pins to be driven into the bone;

modifying such members to be hingedly removably securable to the stabilization bar member;

whereby additional pins can be added to the sequence of pins at pre-selected locations during the bone stabilization procedure.

10. In the method of bone stabilization for use with an apparatus and procedure for the external unilateral fracture fixation, fracture compression or enlargement of human osseous tissue, which apparatus comprises a clamping fork to hold and position threaded bone penetration pins, and multiple fastening slidable means with clamping forks to attach the pins to a slidable member to hold in position the clamping forks, comprising:

means for securing the aforesaid apparatus so that the pins may be moved toward or away from each other, separately shifted longitudinally, separably shifted laterally, and separately shifted upwardly and downwardly; and means for hingedly dividing the clamping portions;

whereby additional pins can be added to the sequence of pins at preselected locations during the original bone stabilization thereafter.

* * * * *